United States Patent [19]

Sato et al.

[11] 4,064,200

[45] Dec. 20, 1977

[54] PROCESS FOR THE PREPARATION OF O,O-DIALKYL-S-BENZYL THIOPHOSPHATES

[75] Inventors: Zenichi Sato, Shimizu; Fumio Shimizu, Shizuoka; Shoji Kusano, Shizuoka; Keiichiro Takagi, Shizuoka; Yoji Imamiya, Shizuoka, all of Japan

[73] Assignee: Ihara Chemical Kogyo Kabushiki Kaisha, Tokyo, Japan

[21] Appl. No.: 648,756

[22] Filed: Jan. 13, 1976

[30] Foreign Application Priority Data

Jan. 17, 1975   Japan .................................... 50-0350

[51] Int. Cl.$^2$ ............................................. C07F 9/165
[52] U.S. Cl. .................................... 260/979; 260/963
[58] Field of Search ........................ 260/985, 987, 979

[56] References Cited

U.S. PATENT DOCUMENTS 2,862,016  11/1958  Sallmann et al. ..................... 260/985
3,636,144  1/1972  Tsuchiya et al. ................. 260/987 X
3,832,425  8/1974  Franke ........................... 260/987 X

FOREIGN PATENT DOCUMENTS 18,367  9/1963  Japan .................................... 260/970

Primary Examiner—Anton H. Sutto
Attorney, Agent, or Firm—Brisebois & Kruger

[57] ABSTRACT

O,O-Dialkyl-S-benzyl thiophosphates are obtained by reacting a diester of phosphorous acid such as dimethyl phosphite or diethyl phosphite, in an organic solvent such as toluene or xylene which is sparingly soluble or insoluble in water, with sulfur and an alkali or alkaline earth metal hydroxide or oxide such as NaOH or Ca(OH)$_2$, extracting the reaction product with water and then reacting the extract with a benzyl halide. In this manner, O,O-dialkyl-S-benzyl thiophosphates useful as agricultural and horticultural bactericidal and insecticidal agents are industrially advantageously obtained in a high purity and in a high yield.

10 Claims, No Drawings

PROCESS FOR THE PREPARATION OF O,O-DIALKYL-S-BENZYL THIOPHOSPHATES

BACKGROUND OF THE INVENTION:

The present invention relates to a process for the preparation of organophosphorus compounds useful as agricultural and horticultural bactericidal and insecticidal agents. More particularly, the present invention relates to an industrially advantageous process for the preparation of organophosphorus compounds, i.e., O,O-dialkyl-S-benzyl thiophosphates, in high purity and efficiency.

Known hitherto as a method for preparing O,O-dialkyl-S-benzyl thiophosphates is the following two-step process. In the first step, a diester of phosphorous acid is reacted according to the following reaction formulas with sulfur and a metal carbonate or ammonium carbonate to prepare a metal salt or ammonium salt of a monothiophosphoric acid diester (Japanese Patent Publn. No. 18367/63).

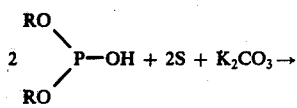

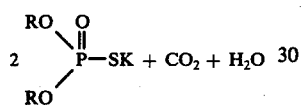

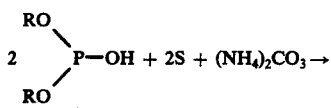

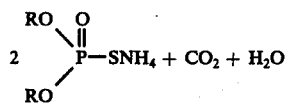

The resultant metal or ammonium salt of a monothiophosphoric acid diester is then reacted according to the following reaction formulas with a benzyl halide to prepare the desired O,O-dialkyl-S-benzyl thiophosphate [Japanese Patent Publn. No. 2968/57; a Japanese book entitled "Chemistry of Agricultural Agents" (a book in industrial chemistry series) compiled by the Chemical Society of Japan and published by Dainihon Tosho K. K., pages 61–62].

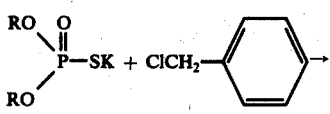

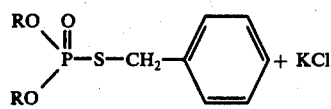

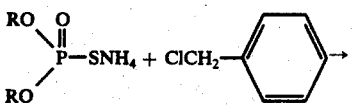

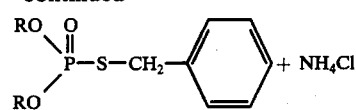

However, one of the largest drawbacks in the known prior process is that the formation of carbon dioxide as by-product is unavoidable, as is evident from the above reaction formulas, during the reaction for preparing a metal or ammonium salt of a monothiophosphoric acid diester. When the reaction is carried out according to the known prior process, a large amount of carbon dioxide is violently evolved as the reaction proceeds so that a bumping phenomenon often takes place during the reaction whereby the reaction solvent and the starting materials are entrained in the evolved carbon dioxide and escape from the reaction system, thus incurring considerable loss of the reaction solvent and the starting materials used. As it is extremely difficult to control evolution of carbon dioxide by adjustment of the reaction temperature, the known prior process is not satisfactory as an industrially applicable process.

Further detrimental drawback in the prior process is that the end product, i.e., O,O-dialkyl-S-benzyl thiophosphate, is contaminated with impurities including sulfur used as the starting material. Accordingly, it is impossible to prepare the desired O,O-dialkyl-S-benzyl thiophosphate in a high purity without necessity of further complicate operations for eliminating the sulfur contaminant.

Many of these drawbacks result from the use of a metal carbonate or ammonium carbonate as one of the starting materials. Thus, the use of a metal hydroxide was proposed in this case to overcome the drawbacks. However, the use of a metal hydroxide easily tends to permit hydrolysis of a diester of phosphorous acid used as the main starting material. In addition, a side reaction tends to occur between a metal hydroxide and sulfur which is another starting material, thus permitting the formation of thiosulfates. For these reasons, the use of a metal hydroxide fails to attain the purpose aimed at. Especially noteworthy is that as alkalinity of a metal hydroxide used becomes stronger, hydrolysis of the diester of phosphorous acid and the side reaction between a metal hydroxide and sulfur will be promoted.

According to our study, it has been found that when the reaction is conducted by using a hydroxide of an alkali metal such as sodium or potassium, the following reactions take place in the prior process:

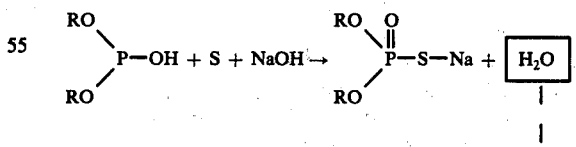

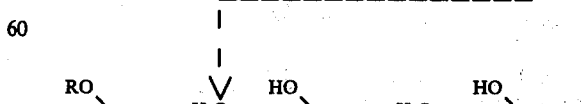

When water exists in the reaction system, the diester of phosphorous acid is rapidly hydrolyzed.

From these facts, it has been believed that alkali metal salts of monothiophosphoric acid diesters cannot be prepared from diesters of phosphoric acid, sulfur and alkali metal hydroxide and that O,O-dialkyl-S-benzyl thiophosphates aimed at cannot be prepared in a good yield.

Further, a method of reacting a diester of phosphorous acid, sulfur and methanol solution of ammonia was proposed. However, the method has a disadvantage that undesired dialkyl ester is obtained as a by-product due to an interesterification.

BRIEF SUMMARY OF THE INVENTION:

In accordance with the present invention, there is provided a process for the preparation of O,O-dialkyl-S-benzyl thiophosphates of the general formula:

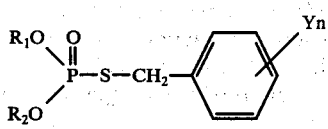

wherein $R_1$ and $R_2$ each stand for an alkyl group with 1–5 carbon atoms and Y for a halogen atom, an alkyl group with 1–4 carbon atoms, an alkoxyl group with 1–4 carbon atoms or a nitro group, and $n$ for zero or an integer of 1–4, with the proviso that when $n$ is an integer of 2–4, Y may be the same or different, characterized by reacting (a) a diester of phosphorous acid of the general formula:

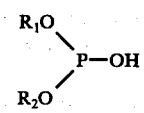

wherein $R_1$ and $R_2$ have the same meanings as given above, in an organic solvent which is sparingly soluble or insoluble in water with (b) sulfur and (c) at least one selected from the group consisting of hydroxides and oxides of alkali and alkaline earth metals, and then reacting an aqueous extract of the resulting reaction product with a benzyl halide of the general formula:

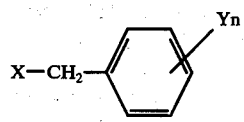

wherein X stands for a halogen atom and Y and $n$ have the same meanings as given above.

It is an object of the present invention to provide an industrially advantageous process for the preparation of O,O-dialkyl-S-benzyl thiophosphates useful as agricultural and horticultural bactericidal and insecticidal agent without permitting occurrence of any side reaction.

It is another object of the present invention to provide a process for the production of O,O-dialkyl-S-benzyl thiophosphates in high purity and yield.

It is still another object of the present invention to provide a process for the preparation of O,O-dialkyl-S-benzyl thiophosphates without accompanying evolution of carbon dioxide.

Other and further objects, features and advantages of the present invention will appear more fully from the following description,

DETAILED DESCRIPTION OF THE INVENTION:

The process of the present invention is shown, for example, by the following reaction formulas:

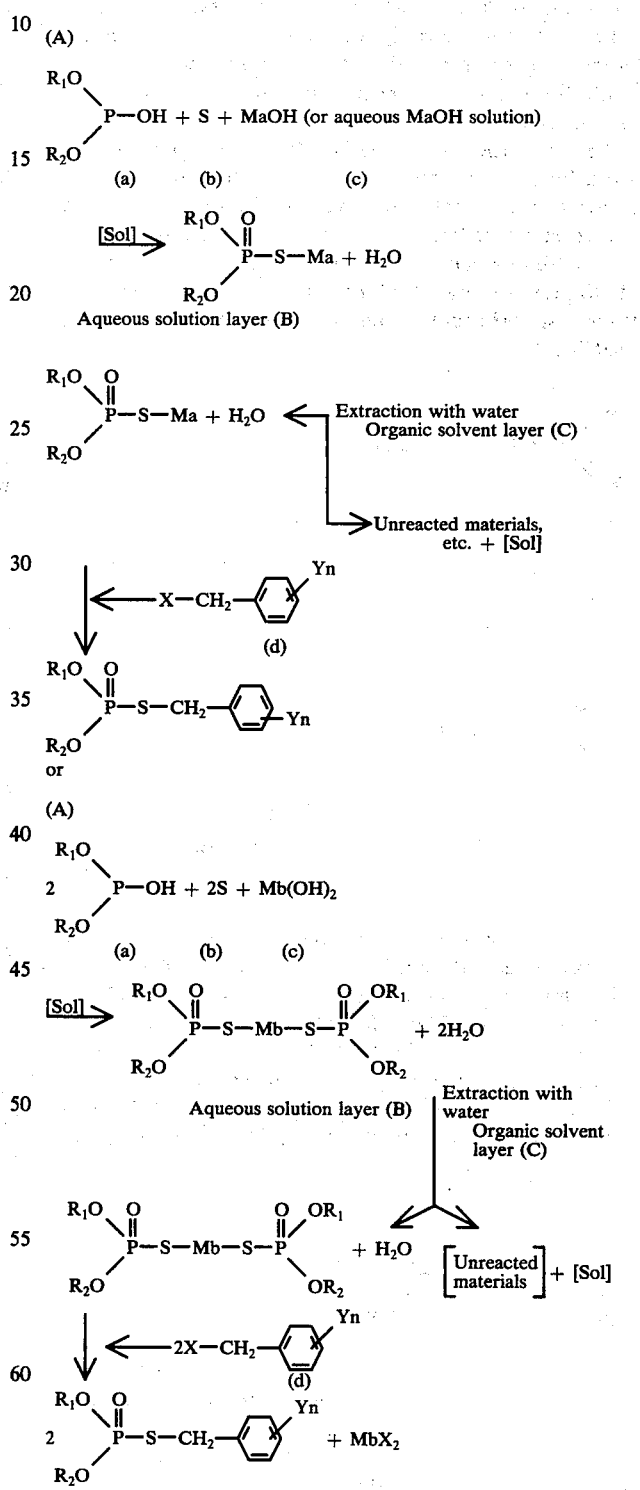

In these reaction formulas, $R_1$, $R_2$, X, Y and $n$ have the same meanings as given above Ma stands for an alkali metal, Mb for an alkaline earth metal and [Sol] for an organic solvent which is sparingly soluble or insoluble in water.

In the process of the present invention, (a) a diester of phosphorous acid is first reacted in an organic solvent sparingly soluble or insoluble in water with (b) sulfur and (c) an alkali or alkaline earth metal hydroxide or oxide.

Examples of (a) a diester of phosphorous acid used in the process of this invention as one of the starting materials include dimethyl phosphite, diethyl phosphite, di-n-propyl phosphite, di-isopropyl phosphite, di-n-butyl phosphite, di-tert-butyl phosphite, di-n-amyl phosphite, di-isoamyl phosphite, O-methyl-O-ethyl phosphite, O-methyl-O-propyl phosphite, O-methyl-O-isopropyl phosphite, O-methyl-O-butyl phosphite, O-ethyl-O-butyl phosphite.

Examples of an alkali metal hydroxide include sodium hydroxide and potassium hydroxide. An aqueous solution of these hydroxides can also be used in the process of the present invention.

Illustrative of a hydroxide of a divalent alkaline earth metal are magnesium hydroxide $Mg(OH)_2$, calcium hydroxide $Ca(OH)_2$ and barium hydroxide $Ba(OH)_2$. Illustrative of an oxide of such alkaline earth metal are magnesium oxide MgO, calcium oxide CaO and barium oxide BaO.

Organic solvents used in the process of this invention which are sparingly soluble or insoluble in water include aliphatic hydrocarbons, ethers, cyclic hydrocarbons, aromatic hydrocarbons and heterocyclic compounds. Illustrative of these organic solvents are n-hexane, isohexane, n-heptane, n-octane, isooctane, n-decane, petroleum ether containing n-hexane as predominant ingredient, ethyl ether, propyl ether, butyl ether, n-amyl ether, decaline, tetraline, benzene, toluene, xylene, ethylbenzene, diethylbenzene, isopropylbenzene, amylbenzene, diamylbenzene and p-cymene. Preferable solvents are those in which solubility of a diester of phosphorous acid and sulfur is high.

Any mode of reaction can be adopted in the present invention for reacting (a) a diester of phosphorous acid in a water insoluble solvent with (b) sulfur and (c) an alkali or alkaline earth metal hydroxide or oxide. In case an alkali metal hydroxide or oxide is used, the reaction is preferably carried out by adding (a) a diester of phosphorous acid and (b) sulfur to an organic solvent and then adding slowly (c) an alkali metal hydroxide or oxide to the solution or adding dropwise thereto an aqueous solution of the alkali metal hydroxide while stirring the solution. In case an alkaline earth metal hydroxide or oxide is used, the reaction is preferably conducted in a manner wherein (b) sulfur and (c) an alkaline earth metal hydroxide or oxide are added to a water insoluble organic solvent and to this mixture under agitation is added dropwise (a) a diester of phosphorous acid or in a manner wherein (a) a diester of phosphorous acid (b) sulfur and (c) an alkaline earth metal hydroxide or oxide are added at the same time to a water insoluble organic solvent and the mixture is stirred.

This reaction is carried out usually under atmospheric pressure. Although the reaction is exothermic, the reaction is carried out at a temperature within a range from 0° C to 100° C, preferably from 10° C to 90° C. If the reaction temperature exceeds 100° 1 C, the ester will undergo hydrolysis. The reaction time required for the reaction after addition of an alkali or alkaline earth metal hydroxide or oxide is usually 0.5-2 hours. In case an alkali metal hydroxide is used as an aqueous solution thereof, its concentration is at least 5%, preferably 5-50%.

In the process of this invention, (a) a diester of phosphorous acid, (b) sulfur and (c) an alkali or alkaline earth metal hydroxide or oxide are used preferably in stoichiometrical amounts. No substantial difference is found when any of the reactants is used in an excess amount. An alkali metal hydroxide or an alkaline earth metal hydroxide or oxide can be used in an amount of 0.1-0.9% excess. Sulfur can be used in an amount of 1-10% excess. When sulfur is used excessively, an excess amount of sulfur can be recovered after completion of the reaction by removing a water insoluble organic solvent under reduced pressure. The recovered sulfur may of course be employed again for the reaction.

After reacting (a) a diester of phosphorous acid with (b) sulfur and (c) an alkali or alkaline earth metal hydroxide or oxide, water is added to the reaction liquid and the mixture is shaken or stirred vigorously whereby the resultant alkali or alkaline earth metal salt of monothiophosphoric acid diester is easily taken up in the aqueous phase. In this extraction treatment, water is preferably used in such an amount that the concentration of the resultant alkali metal or alkaline earth metal salt is at most about 40%. The extraction treatment is usually carried out at a temperature ranging from 10° C to 80° C.

In the process of this invention, the subsequent reaction is carried out after the above extraction treatment with water has been finished. Accordingly, the product obtained in the first reaction step is not contaminated with sulfur, thus resulting in remarkable enhancement in purity and quality of the end product.

In the event the subsequent reaction is carried out without effecting the extraction treatment with water, excess sulfur will remain in the product and cause the following troublesome problems: (1) the end product is colored, (2) sulfur precipitates even after repeated filtration, (3) the purity of the end product is lowered by 0.5-1.0%, and (4) recovery of the solvent used is necessary after the final stage of the reaction.

The aqueous solution layer (B) separated by extraction is distilled under reduced pressure to isolate the alkali or alkaline earth metal salt of monothiophosphoric acid diester which is then reacted with (d) a benzyl halide. Alternatively, (d) a benzyl halide is directly added to the aqueous solution layer (B) and the mixture is heated under agitation whereby the reaction proceeds satisfactorily to produce the desired O,O-dialkyl-S-benzyl thiophosphate in a good yield.

In case the reaction is performed by adding (d) a benzyl halide to the aqueous solution layer (B), the reaction is preferablyconducted at a temperature within a range of 20°-100° C, preferably 50°-90° C. The reaction time required for completion of this reaction is 1-3 hours. Both reactants are preferably used in a molar ratio of 1 : 1.

Described below are the character and technical merits of the process of the present invention.

Firstly, hydrolysis of the diester of phosphorous acid used and any side reaction with sulfur are satisfactorily inhibited and the desired O,O-dialkyl-S-benzyl thiophosphate can be prepared in a good yield by performing the reaction of the diester with sulfur and an alkali or alkaline earth metal hydroxide or oxide in an organic solvent which is sparingly soluble or insoluble in water, in spite of using a strongly alkaline reactant, i.e., an alkali or alkaline earth metal hydroxide or oxide.

Secondly, the reaction permits no evolution of troublemaking carbon dioxide during the reaction since there is no necessity of using a metal carbonate or ammonium carbonate as alkaline reagent.

Thirdly, unreacted materials such as sulfur and/or by-products which cause lowering of the purity can be removed and the desired O,O-dialkyl-S-benzyl-thiophosphate can be prepared in a high purity by interposing an extraction treatment with water after the reaction of the diester of phosphorous acid with sulfur and an alkali or alkaline earth metal hydroxide or oxide.

Finally, the process of the present invention produces no undesired dialkyl thiophosphate as a by-product by interesterification.

To further illustrate the present invention, and not by way of limitation, the following examples and comparative examples are given.

EXAMPLE 1

Preparation of O,O-di-isopropyl-S-benzyl thiophosphate

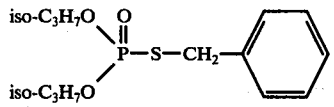

1. In a four-necked flask equipped with a stirrer, a thermometer and a reflux condenser were placed 300 ml of toluene to which were then added 166.0g (1.0 mol) of di-isopropyl phosphite and 33.6g (1.05 mols) of powdery sulfur. To the mixture were added dropwise 83.3g (1.0 mol) of a 48% aqueous solution of sodium hydroxide over a period of 30 minutes while stirring and cooling the mixture.

When the aqueous solution of sodium hydroxide was added dropwise, an exothermic reaction took place and the reaction temperature was rapidly elevated. Thus, the aqueous solution of sodium hydroxide was added dropwise in such manner that the reaction temperature was controlled within a range from 18° C to 58° C by cooling the flask with ice.

The reaction liquid was in the form of a yellow slurry at the time of initiating the reaction. As sulfur was dissolved in the liquid with the proceeding of the reaction, the reaction liquid became a light yellow transparent homogeneous solution as the time of completion of the reaction. After addition of the aqueous solution of sodium hydroxide, the reaction was continued for one hour while controlling the reaction temperature within a range from 55° C to 60° C.

After completion of the reaction, the reaction liquid was removed to a separating funnel. After addition of 200ml of water to the liquid, the mixture was well shaken and then the aqueous phase was separated from the organic phase. After addition of 100ml of water to the organic phase, the mixture was again shaken and the aqueous phase was separated. By the extraction treatment with water, the product was taken up in the aqueous phase. (2) In a four-necked flask equipped with a stirrer, a thermometer and a reflux condenser was placed the aqueous phase extracted. After addition of 122.8g (0.97 mol) of benzyl chloride to the aqueous phase, the mixture was reacted for one hour at 80° C.

After completion of the reaction, the organic phase of the reaction liquid was extracted three times each with 100ml of ether. The ethereal extract was then washed with water and dried over anhydrous sodium sulfate. After removing ether by distillation under reduced pressure, the residual liquid was distilled by the aid of a mercury diffusion pump whereby 265.4g (yield: 95.0%) of O,O-di-isopropyl-S-benzyl thiophosphate were obtained as a colorless transparent liquid having a boiling point of 120.0°-125.0° C/0.05mmHg.

EXAMPLE 2

Isolation of sodium di-isopropyl-mpnothiophosphate

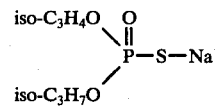

The reaction was carried out in a manner similar to that described in Example 1 (1), and the aqueous extract obtained after completion of the reaction was concentrated, cooled and allowed to stand whereby 213.4g (yield: 97.0%) of sodium di-isopropyl-monothiophosphate were isolated as white crystals having a melting point of 220°-226° C.

COMPARATIVE EXAMPLE 1

In the process described in Example 1 (1), toluene was not employed but di-isopropyl phosphite and sulfur were added to 100ml of water and the reaction was carried out by adding dropwise an aqueous solution of sodium hydroxide to the mixture under agitation. The reaction liquid was filtered to remoe unreacted sulfur. A given amount of benzyl chloride was added to the resultant reaction solution and the mixture was reacted whereby 82.3g (yield: 29.5%) of the desired O,O-di-isopropyl-S-benzyl thiophosphate were obtained.

EXAMPLE 3

The reaction was carried out in a manner similar to that described in Example 1 (1) except that 40.0g (1.0 mol) of solid sodium hydroxide were used in place of a 48% aqueous solution of sodium hydroxide. The reaction product was then reacted with benzyl chloride in a manner similar to that described in Example 1 (2) whereby 259.8g (yield: 93.0%) of O,O-di-isopropyl-S-benzyl thiophosphate were obtained.

EXAMPLE 4

In a manner similar to that described in Example 1 (1) and (2), various (a) diesters of phosphorous acid were reacted in an organic solvent sparingly soluble or insoluble in water with (b) sulfur and various (c) alkali metal hydroxide at a regulated reaction temperature $T_1$, and the resulting reaction liquid was extracted with water and finally the aqueous extract was reacted with various (d) benzyl halide at a reaction temperature $T_2$ to prepare various O,O-dialkyl-S-benzyl thiophosphates. Results obtained are shown in Table 1.

COMPARATIVE EXAMPLE 2

The reaction was carried out according to the process of Example 4 (1) except that 100 ml of water used in place of 400 ml of toluene. A result of the reaction is shown as Comparative Example 2 also in Table 1.

Table 1

| Exp. No. | (a) Diester of phosphorous acid (Amount used) | Amount of (b) sulfur used | (c) MOH (Amount used) | $T_1$(°C) (Time) | Org. solvent (Amount used) | (d) Benzyl halide (Amount used) | $T_2$ (°C) | Product (Boiling point: °C/mmHg) | Amount of Product (Yield) |
|---|---|---|---|---|---|---|---|---|---|
| 1 Comp. Ex. 2 | (C₂H₅O)₂P(=O)—OH (138.1g) | 33.6g | NaOH 48% Aq. sol. (83.3g) | 10–20 (3 hrs.) | Toluene (400 ml) / Water (100 ml) | Cl—CH₂—C₆H₅ (126.5g) | 50 | (C₂H₅O)₂P(=O)—S—CH₂—C₆H₅ Colorless transparent liquid (140–145/1–2) | 220.9g (84.9%) 74.5g (28.5%) |
| 2 | (C₂H₅O)₂P(=O)—OH (138.1g) | 33.6g | KOH 40% Aq. sol. (135.0g) | 10–20 (3 hrs.) | Toluene (400 ml) | Cl—CH₂—C₆H₃Cl₂ (195.5g) | 50 | (C₂H₅O)₂P(=O)—S—CH₂—C₆H₃Cl₂ Yellow transparent liquid (131–135/0.02) | 207.3g (81.5%) |
| 3 | (C₂H₅O)₂P(=O)—OH (138.1g) | 33.6g | KOH Solid (54.0g) | 16–20 (3 hrs.) | Toluene (400 ml) | Cl—CH₂—C₆HCl₄ (264.4g) | 50 | (C₂H₅O)₂P(=O)—S—CH₂—C₆HCl₄ Light yellow transparent liquid (167–170/0.01) | 312.0g (78.2%) |
| 4 | (C₂H₅O)₂P(=O)—OH (138.1g) | 33.6g | NaOH 48% Aq. sol. (83.3g) | 10–20 (3 hrs.) | Benzene (400 ml) | Cl—CH₂—C₆H₄—OCH₃ (156.5g) | 50 | (C₂H₅O)₂P(=O)—S—CH₂—C₆H₄—OCH₃ Yellow transparent liquid ($n_D^{20}$ 1.6645 ... Refractive index) | 241.5g (83.2%) |
| 5 | (C₂H₅O)₂P(=O)—OH (138.1g) | 33.6g | NaOH 48% Aq. sol. (83.3g) | 10–20 (3 hrs.) | Benzene (400 ml) | Cl—CH₂—C₆H₃(CH₃)(NO₂) (188.5g) | 50 | (C₂H₅O)₂P(=O)—S—CH₂—C₆H₃(CH₃)(NO₂) Yellow transparent liquid (164–170/0.025) | 255.9g (79.1%) |
| 6 | (CH₃O)(iso-C₃H₇O)P(=O)—OH (138.1g) | 33.6g | NaOH 48% Aq. sol. (83.3g) | 10–20 (3 hrs.) | Xylene (400 ml) | Cl—CH₂—C₆H₄—Cl (161.0g) | 50 | (CH₃O)(iso-C₃H₇O)P(=O)—S—CH₂—C₆H₄—Cl Colorless transparent liquid (120–125/0.01) | 237.2g (80.1%) |
| 7 | (iso-C₃H₇O)₂P(=O)—OH (166.0g) | 33.6g | KOH 40% Aq. sol. (135.9g) | 20–50 (0.5 hr) | Xylene (300 ml) | Br—CH₂—C₆H₄—Cl (205.4g) | 50 | (iso-C₃H₇O)₂P(=O)—S—CH₂—C₆H₄—Cl Yellow transparent liquid (45/0.05) | 305.4g (95.0%) |

Table 1-continued

| Exp. No. | (a) Diester of phosphorous acid (Amount used) | Amount of (b) sulfur used | (c) MOH (Amount used) | $T_1$ (°C) (Time*) | Org. solvent (Amount used) | (d) Benzyl halide (Amount used) | $T_2$ (°C) | Product (Boiling point: °C/mmHg) | Amount of Product (Yield) |
|---|---|---|---|---|---|---|---|---|---|
| 8 | (n-C$_4$H$_9$O)$_2$P—OH (194.2g) | 33.6g | NaOH solid (40.0g) | 20-50 (0.5 hr) | Xylene (300 ml) | Br—CH$_2$—C$_6$H$_5$ (171.0g) | 50 | (n-C$_4$H$_9$O)$_2$P(=O)—S—CH$_2$—C$_6$H$_5$ Yellow transparent liquid (142-145/0.01) | 291.4g (92.1%) |
| 9 | (n-C$_5$H$_{11}$O)$_2$P—OH (222.2g) | 33.6g | NaOH 48% Aq. sol. (83.3g) | 20-50 (0.5 hr) | Toluene (300 ml) | Cl—CH$_2$—C$_6$H$_5$ (126.5g) | 80 | (n-C$_5$H$_{11}$O)$_2$P(=O)—S—CH$_2$—C$_6$H$_5$ Light yellow transparent liquid (140/0.01) | 310.6g (90.2%) |

This table obviously shows that according to the process of this invention O,O-dialkyl-S-benzyl thiophosphates are obtained in a high yield and in a high purity.

EXAMPLE 5

Preparation of O,O-diethyl-S-benzyl thiophosphate

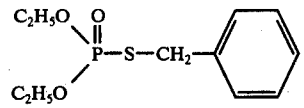

In a four-necked flask equipped with a stirrer, a thermometer and a reflux condenser were placed 300 ml of benzene. After addition of 138.0g (0.99 mol) of diethyl phosphite, 32.7g (1.02 mols) of powdery sulfur and 38.5g (0.52 mol) of calcium hydroxide to the benzene, the mixture was reacted for one hour at 80°-85° C with stirring.

The reaction liquid was in the form of a yellow slurry at the time of initiating the reaction. As sulfur was dissolved in the liquid with the proceeding of the reaction, the reaction liquid became a light yellow transparent solution at the time of completion of the reaction.

After completion of the reaction, the reaction liquid was removed to a separating funnel where the reaction liquid was admixed with 200 ml of water and the aqueous phase was separated. The organic phase was further admixed with 100 ml of water and the aqueous phase was separated. By this extraction treatment with water, the product was taken up in the aqueous phase.

The aqueous extract was then placed in a four-necked flask equipped with a stirrer, a thermometer and a reflux condenser. After addition of 126.5g (0.99 mol) of benzyl chloride to the aqueous extract, the mixture was reacted for one hour at 80° C.

After completion of the reaction, the organic phase of the reaction liquid was extracted three times each with 100 ml of ether.

The ethereal extract was then washed with water and dried over anhydrous sodium sulfate. After removing ether by distillation under reduced pressure, the residual liquid was distilled by the aid of a mercury diffusion pump whereby 228.8g (yield: 87.8%) of O,O-diethyl-S-benzyl thiophosphate were obtained as a colorless transparent liquid having a boiling point of 127°-131° C/0.3-0.4 mmHg.

EXAMPLE 6

Isolation of bis(di-isopropyl-monothiophosphato)calcium

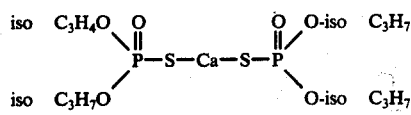

In a manner similar to that discribed in Example 1 (1), 83g (0.49 mol) of di-isopropyl phosphite was reacted in 200 ml of toluene with 16g (0.26 mol) of powdery sulfur and 19g (0.26 mol) of calcium hydroxide for 2 hours at 80°-90° C. Thus 98.7g (yield: 91.2%) of bis(di-isopropyl-monothiophosphato)calcium were isolated as white crystals having a metling point of 98°-110° C.

EXAMPLE 7

In a manner similar to that described in Example 5, 138.0g (0.99 mol) of diethyl phosphite was reacted in 300 ml of toluene with 32.7g (1.02 mols) of powdery sulfur and 28.8g (0.51 mol) of calcium oxide for 1 hour at 85°-90° C.

After completion of the reaction, the reaction liquid was removed to a separating funnel where the reaction liquid was admixed with 200 ml of water and the aqueous phase was separated. The organic phase was further admixed with 100 ml of water and the aqueous phase was separated. By this extraction treatment with water, the product was taken up in the aqueous phase.

The aqueous extract was then placed in a four-necked flask equipped with a stirrer, a thermometer and a reflux condenser. After addition of 169.3g (0.99 mol) of benzyl bromide to the aqueous extract, the mixture was reacted for one hour at 80° C. After completion of the reaction, the reaction mixture was subjected to an after-treatment similar to that described in Example 5 whereby 231.5g (89.0%) of O,O-diethyl-S-benzyl thiophosphate were obtained.

COMPARATIVE EXAMPLE 3

The reaction was carried out according to the process of Example 7 except that calcium carbonate was used in place of calcium oxide.

Namely, 300 ml of toluene were placed in a four-necked flask equipped with a stirrer, a thermometer and a reflux condenser. After addition of 138.0g (0.99 mol) of diethyl phosphite, 32.0g (0.99 mol) of powdery sulfur and 50.0g (0.49 mol) of calcium carbonate to the toluene, the mixture was gradually heated with stirring from room temperature to 100° C. With the proceeding of the reaction, carbon dioxide was violently evolved and sulfur was dissolved. After lapse of 3 hours, evolution of carbon dioxide was ceased and the reaction liquid became a yellow transparent solution. The temperature of the reaction liquid was then elevated to 110°-115° C and the reaction liquid was stirred for 1 hour to complete the reaction.

After completion of the reaction, the extraction treatment with water was carried out in a manner similar to that described in Example 5 and the aqueous extract was reacted with 126.5g (0.99 mol) of benzyl chloride for 4 hours at 80° C. The reaction mixture was then subjected to the after-treatment whereby 117.3g (yield: 45.1%) of O,O-diethyl-S-benzyl thiophosphate were obtained.

EXAMPLE 8

In a manner similar to that described in Example 5, various (a) diesters of phosphorous acid were reacted in an inert solvent [Sol] with (b) sulfur and (c) a bivalent alkaline earth metal hydroxide $M(OH)_2$ or oxide MO at a regulated reaction temperature $T_1$, and the resulting reaction liquid was extracted with water and finally the aqueous extract was reacted with (d) a benzyl halide at a regulated reaction temperature $T_2$ to prepare various O,O-dialkyl-S-benzyl thiophosphates. Results obtained are shown in Table 2.

Table 2

| Exp. No. | (a) Diester of phosphorous acid (Amount used) | Amount of (b) sulfur used | (c) M(OH)₂ (Amount used) | (c) MO (Amount used) | [Sol] (Amount used) | T₁ °C | (d) Benzyl halide (Amount used) | T₂ °C | Product (Boiling point: °C/mmHg) | Amount of product (Yield) |
|---|---|---|---|---|---|---|---|---|---|---|
| 1 | (CH₃O)₂P(O)H (110.0g) | 32.0g | — | CaO (28.0g) | Toluene (300 ml) | 80–85 | p-Cl-C₆H₄-CH₂Cl (159.0g) | 80 | (CH₃O)₂P(O)-S-CH₂-C₆H₄-Cl (130–132/0.03) | 234.1g (87.8%) |
| 2 | (C₂H₅O)₂P(O)H (138.0g) | 32.0g | Ca(OH)₂ (37.0g) | — | Toluene (300 ml) | 80–85 | o-NO₂-C₆H₄-CH₂Cl (170.0g) | 80 | (C₂H₅O)₂P(O)-S-CH₂-C₆H₄-NO₂ (143–144/0.001) | 244.9g (80.3%) |
| 3 | (C₂H₅O)₂P(O)H (138.0g) | 32.0g | Ca(OH)₂ (37.0g) | — | Toluene (300 ml) | 80–85 | p-CH₃O-C₆H₄-CH₂Cl (154.0g) | 80 | (C₂H₅O)₂P(O)-S-CH₂-C₆H₄-OCH₃ (Refractive index: n₂₀ 1.6650) | 235.4g (81.1%) |
| 4 | (C₂H₅O)₂P(O)H (138.0g) | 32.0g | Ca(OH)₂ (37.0g) | — | p-Xylene (300 ml) | 80–85 | o-Cl-C₆H₄-CH₂Cl (159.0g) | 80 | (C₂H₅O)₂P(O)-S-CH₂-C₆H₄-Cl (112–118/0.01) | 259.2g (88.0%) |
| 5 | (C₂H₅O)₂P(O)H (138.0g) | 32.0g | — | CaO (28.0g) | Benzene (300 ml) | 80–85 | 3,4-Cl₂-C₆H₃-CH₂Cl (193.0g) | 90 | (C₂H₅O)₂P(O)-S-CH₂-C₆H₃-Cl₂ | 288.6g (87.7%) |
| 6 | (iso-C₃H₇O)₂P(O)H (83.1g) | 16.0g | Ca(OH)₂ (19.0g) | — | Toluene (200 ml) | 80–85 | C₆H₅-CH₂Cl (64.0g) | 80 | (iso-C₃H₇O)₂P(O)-S-CH₂-C₆H₅ (150–155.01) | 127.7g (88.7%) |
| 7 | (iso-C₃H₇O)₂P(O)H (83.0g) | 16.0g | — | BaO (40.0g) | n-Hexane (200 ml) | 65–70 | o-NO₂-C₆H₄-CH₂Cl (170.0g) | 80 | (iso-C₃H₇O)₂P(O)-S-CH₂-C₆H₄-NO₂ (118–120/0.005) | 123.9g (86.0%) |
| 8 | (n-C₄H₉O)₂P(O)H (97.0g) | 16.0g | Ba(OH)₂ (43.8g) | — | Benzene (200 ml) | 80–85 | C₆H₅-CH₂Cl (64.0g) | 80 | (n-C₄H₉O)₂P(O)-S-CH₂-C₆H₅ (116–119/0.001) (120–130/0.1–0.15) | 134.3g (84.9%) |

As is evident from the table, a variety of O,O-dialkyl-S-benzyl thiophosphates are obtained according to the process of this invention in a high yield. In addition, these products are of high purity.

What is claimed is:

1. A process for the preparation of O,O-dialkyl-S-benzyl thiophosphates of the general formula:

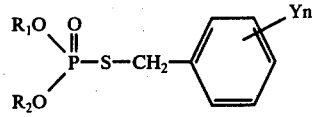

where in $R_1$ and $R_2$ each stand for an alkyl group with 1–5 carbon atoms and Y for halogen, an alkyl with 1–4 carbon atoms, and alkoxyl with 1–4 carbon atoms or a nitro group, and $n$ for zero or an integer of 1–4, with the proviso that when $n$ is an integer of 2–4, Y may be the same or different, characterized by reacting (a) a diester of phosphorous acid of the general formula:

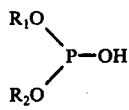

wherein $R_1$ and $R_2$ have the same meanings as given above, in an organic solvent which is sparingly soluble or insoluble in water with (b) sulfur and (c) at least one compound selected from the group consisting of hydroxides and oxides of alkali and alkaline earth metals, and then reacting an aqueous extract of the resulting reaction product with a benzyl halide of the general formula:

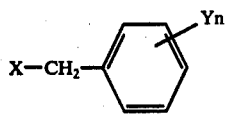

wherein X stands for halogen and Y and $n$ have the same meanings given above.

2. A process according to claim 1 wherein said organic solvent which is sparingly soluble or insoluble in water is at least one selected from the group consisting of n-hexane, isohexane, n-heptane, n-octane, isooctane, n-decane, petroleum ether containing n-hexane as predominant ingredient, ethyl ether, propyl ether, butyl ether, n-amyl ether, decaline, tetraline, benzene, toluene, xylene, ethylbenzene, diethylbenzene, isopropylbenzene, amylbenzene, diamylbenzene and p-cymene.

3. A process according to claim 1 wherein the alkali or alkaline earth metal hydroxide or oxide is at least one selected from the group consisting of NaOH, KOH, $Mg(OH)_2$, $Ca(OH)_2$, $Ba(OH)_2$, MgO, CaO and BaO.

4. A process according to claim 1 wherein said diester of phosphorous acid is at least one selected from the group consisting of dimethyl phosphite, diethyl phosphite, di-n-propyl phosphite, di-isopropyl phosphite, di-n-butyl phosphite, di-tert-butyl phosphite, di-n-amyl phosphite, di-isoamyl phosphite, O-methyl-O-ethyl phosphite, O-methyl-O-propyl phosphite, O-methyl-O-isopropyl phosphite, O-methyl-O-butyl phosphite and O-ehyl-O-butyl phosphite.

5. A process according to claim 1 wherein said alkali metal hydroxide is used as an aqueous solution thereof having a concentration of 5–50%.

6. A process according to claim 1 wherein (a) a diester of phosphorous acid, (b) sulfur, (c) at least one selected from the group consisting of hydroxides and oxides of alkali and alkaline earth metal and (d) a benzyl halide are reacted in an approximately stoichiometrical molar ratio.

7. A process according to claim 1 wherein (a) a diester of phosphorous acid is reacted with (b) sulfur and (c) at least one selected from the group consisting of hydroxides and oxides of alkali and alkaline earth metals at 0°–100° C.

8. A process according to claim 1 wherein (b) sulfur is used in an amount of 1–10% excess.

9. A process according to claim 1 wherein the extraction treatment with water is conducted at 10°–80° C.

10. A process according to claim 1 wherein said aqueous extract at most contains the resulting product in an amount of about 40%.

* * * * *

UNITED STATES PATENT AND TRADEMARK OFFICE
CERTIFICATE OF CORRECTION

PATENT NO. : 4,064,200
DATED : December 20, 1977
INVENTOR(S) : Zenichi SATO et al.

It is certified that error appears in the above-identified patent and that said Letters Patent are hereby corrected as shown below:

[30] Foreign Application Priority Data

January 17, 1975    Japan......50-7503

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*